United States Patent
Tallo Domínguez et al.

(10) Patent No.: US 12,208,163 B2
(45) Date of Patent: Jan. 28, 2025

(54) NANOSTRUCTURED LIPID GEL, METHOD FOR PREPARATION AND USE

(71) Applicant: CONSEJO SUPERIOR DE INVESTIGACIONES CIENTÍFICAS, Madrid (ES)

(72) Inventors: Kirian Tallo Domínguez, Barcelona (ES); Olga Lopez Serrano, Barcelona (ES); Veronica Moner Del Moral, Barcelona (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 868 days.

(21) Appl. No.: 17/285,281

(22) PCT Filed: Oct. 15, 2019

(86) PCT No.: PCT/ES2019/070699
§ 371 (c)(1),
(2) Date: Apr. 14, 2021

(87) PCT Pub. No.: WO2020/079302
PCT Pub. Date: Apr. 23, 2020

(65) Prior Publication Data
US 2021/0361569 A1 Nov. 25, 2021

(30) Foreign Application Priority Data
Oct. 15, 2018 (ES) ................ ES201830989

(51) Int. Cl.
| A61K 9/127 | (2006.01) |
| A61K 9/00 | (2006.01) |
| A61K 9/06 | (2006.01) |
| A61K 31/20 | (2006.01) |
| A61K 31/683 | (2006.01) |
| A61K 45/06 | (2006.01) |
| A61K 47/12 | (2006.01) |
| A61K 47/24 | (2006.01) |
| A61K 49/00 | (2006.01) |

(52) U.S. Cl.
CPC .............. *A61K 9/06* (2013.01); *A61K 9/0014* (2013.01); *A61K 9/0048* (2013.01); *A61K 9/127* (2013.01); *A61K 45/06* (2013.01); *A61K 47/12* (2013.01); *A61K 47/24* (2013.01); *A61K 49/0043* (2013.01); *A61K 49/0052* (2013.01)

(58) Field of Classification Search
None
See application file for complete search history.

(56) References Cited

U.S. PATENT DOCUMENTS

| 4,235,871 A | * | 11/1980 | Papahadjopoulos | C12N 1/04 424/234.1 |
| 4,247,411 A | * | 1/1981 | Vanlerberghe | A61K 8/66 424/193.1 |
| 4,485,054 A | * | 11/1984 | Mezei | A61K 9/1277 436/829 |
| 4,610,868 A | * | 9/1986 | Fountain | A61K 9/127 424/9.4 |
| 5,234,767 A | | 8/1993 | Wallach | |
| 6,207,186 B1 | | 3/2001 | Safinya et al. | |
| 2005/0287180 A1 | | 12/2005 | Chen | |
| 2012/0202882 A1 | | 8/2012 | Banov et al. | |

FOREIGN PATENT DOCUMENTS

| EP | 2163236 A2 | 3/2010 |
| EP | 2210589 A1 | 7/2010 |
| WO | 2006002050 A1 | 1/2006 |
| WO | 2006122638 A1 | 11/2006 |
| WO | 2010102770 A1 | 9/2010 |
| WO | 2011101153 A1 | 8/2011 |

OTHER PUBLICATIONS

Castangia, Ines, et al. "Effects of ethanol and diclofenac on the organization of hydrogenated phosphatidylcholine bilayer vesicles and their ability as skin carriers." Journal of Materials Science: Materials in Medicine 26 (2015): 1-9. (Year: 2015).*
Manconi M, Isola R, Falchi AM, Sinico C, Fadda AM. Intracellular distribution of fluorescent probes delivered by vesicles of different lipidic composition. Colloids and Surfaces B: Biointerfaces. Jun. 15, 2007;57(2):143-51. (Year: 2007).*
Srisuk P, Thongnopnua P, Raktanonchai U, Kanokpanont S. Physicochemical characteristics of methotrexate-entrapped oleic acid-containing deformable liposomes for in vitro transepidermal delivery targeting psoriasis treatment. International journal of pharmaceutics. May 10, 2012;427(2):426-34. (Year: 2012).*
Elnaggar YS, El-Refaie WM, El-Massik MA, Abdallah OY. Lecithin-based nanostructured gels for skin delivery: an update on state of art and recent applications. Journal of controlled release. Apr. 28, 2014;180:10-24. (Year: 2014).*
Tallo et al., "Vesicular nanostructures composed of oleic acid and phosphatidylcholine: Effect of pH and molar ratio", Elsevier, Chemistry and Physics of Lipids, vol. 213, 2018, pp. 96-101, 6 pages.
Kurniawan et al., "Interaction forces and membrane charge tunability: Oleic acid containing membranes in different pH conditions", Elsevier, Biochimical Biophysics Acta, 2017, vol. 2, pp. 211-217, 7 pages.

(Continued)

*Primary Examiner* — Nissa M Westerberg
(74) *Attorney, Agent, or Firm* — Hayes Soloway P.C.

(57) ABSTRACT

The invention relates to a nanostructured lipid gel formed by alternating layers and vesicles composed of phospholipids, fatty acids and a high water content. The structure and fluidity respond reversibly to temperature and pH, and they are capable of transporting at least one active ingredient within the skin and also to the follicles. The exclusively lipid composition ensures high biocompatibility, and the rheological behaviour facilitates topical and ocular application.

15 Claims, 5 Drawing Sheets
(5 of 5 Drawing Sheet(s) Filed in Color)

(56) References Cited

OTHER PUBLICATIONS

Rydhag and Wilton, "The function of phospholipids of soybean lecithin in emulsions", Springer, Journal of the American Oil Chemists' Society, 1981, vol. 58, pp. 830-837, 8 pages.

Warriner et al., "Lamellar Biogels: Fluid-Membrane-Based Hydrogels Containing Polymer Lipids", JSTOR, Science, New Series, 1996, vol. 271, Issue 5251, pp. 969-973, 6 pages.

* cited by examiner

NANOSTRUCTURED LIPID GEL, METHOD FOR PREPARATION AND USE

CROSS-REFERENCE TO RELATED APPLICATIONS AND PRIORITY

This patent application claims priority from PCT Patent Application No. PCT/ES2019/070699 filed Oct. 15, 2019, which claims priority from Spanish Patent Application No. P201830989 filed Oct. 15, 2018. Each of these patent applications are herein incorporated by reference in their entirety.

The present invention belongs to the sector of topical and ocular formulations with potential biomedical applications.

The object of the invention is a nanostructured lipid gel formed by interspersing lamellae and vesicles composed of phospholipids, fatty acids and a high water content. The structure and fluidity thereof respond reversibly to temperature and pH and are capable of transporting at least one hydrophilic substance within the skin and also to the follicles. Their particular organisation, with part of the water trapped in vesicles and these vesicles trapped or interspersed between extended laminae, makes them very adequate as systems for incorporating molecules of a different polar nature in different compartments. Their exclusively lipid composition ensures high biocompatibility and their rheological behaviour enables the easy topical and ocular application thereof.

The method for preparing the aforementioned gels and their use in topical and ocular applications constitutes another object of the present invention.

BACKGROUND OF THE INVENTION

Dense emulsion/gel-type systems constituted by lipids are usually formed at only high lipid concentrations (>50%), generating tight packing phases such as cubic or lamellar phases [L. Rydhag, I. Wilton, *The function of phospholipids of soy lecithin in emulsions*, J. Am. Oil Chem. Soc. 58 (1981) 830-837].

The most diluted systems require other compounds such as surfactants, gelling agents or polymers to achieve gelification [H. E. Warriner, S. H. J. Idziak, N. L. Slack, P. Davidson, C. R. Safinya, *Lamellar Biogels: Fluid-Membrane-Based Hydrogels Containing Polymer Lipids*, Science 271 (1996) p. 969-973][U.S. Pat. No. 6,207,186].

These compounds reduce the biocompatibility of the systems and may cause sensitisations and adverse reactions in biomedical applications.

Other documents of interest and that reflect the state of the art are:

WO2006/122638, which relates to hyaluronic acid or derivatives thereof structured into liposomes to repair skin and soft tissue defects.

In this document there is no reference to the use of fatty acids in the composition of the lipid phase or the proportion of water.

ES2423760 describes a method for manufacturing a basic cosmetic composition which includes coating liposomes with a particle size of 250-600 nm in an aqueous gel with a viscosity in the range of 4,000 to 20,000 mPa·s, which include in their aqueous volume three or four liposomes respectively containing at least one active substance in their aqueous volume, wherein the active substances contained in the included liposomes differ from each other and the included liposomes have a particle size in the range of 50-200 nm. The three or four liposomes are introduced by agitation in water and, next, a liposome-forming agent, a gelling agent and a neutralising product are introduced in the water and liposome mixture. The liposome-forming agents mentioned include, inter alia, lecithin and phosphatidylcholine, but the presence of fatty acids is not mentioned.

Document WO2006/002050 discloses an injectable non-liposomal composition to be used as a tissue filler in the form of a gel or paste comprising a phospholipid component in a range comprised between 10% and 90% of the total weight of the composition. No reference is made to the presence of a fatty acid in the lipid composition which is present in a range of 10% to 90%.

In document EP2210589 the object of the invention is a pharmaceutical composition for the controlled release of an active component which comprises a vesicular phospholipid gel with packed liposomes. The percentage of phospholipids in the composition is, at least, 30% and no mention is made of the presence of fatty acids.

WO2011/101153 claims liposomes containing cosmetic or dermopharmaceutically active and adjuvant ingredients bound to cationic polymers. Regardless of the phospholipid in the liposome composition, there is always the presence of a polymer.

The paper by Talló, K; López, O. and col. *Vesicular nanostructures composed of oleic acid and phosphatidylcholine: Effect of pH and molar ratio*; Chemistry and Physics of Lipids 213 (2018) 96-101 relates to nanostructured systems formed from hydrogenated soy phosphatidylcholine and oleic acid. It was observed that alkaline mediums and high proportions of oleic acid increased membrane fluidity. The product obtained is a liquid dispersion. In this article, the term "gel" makes reference to the gel phase, also known as the crystalline or solid phase of the lipid membranes. This does not mean that the system behaves macroscopically like a gel, but rather that the hydrocarbonated chains are molecularly packed, giving the system-forming membranes greater rigidity.

DESCRIPTION OF THE INVENTION

The object of the present invention is a nanostructured lipid gel formed by interspersing laminae and vesicles.

In the context of the present invention, the term "nanostructured gel" shall be understood as relating to materials with a gel-type rheological behaviour which are organised with at least one dimension smaller than 100 nm. It has also been observed that they are organised on a micro scale. That is, they are organised both on a nano and micro scale.

As opposed to most of the scientific methods reflected in the discussion of the state of the art, in the present invention the nanostructured gel can be formed with a low lipid content, without need for the intervention of polymers or surfactants to favour dispersion.

The first aspect of the present invention is a nanostructured lipid gel formed by interspersing laminae and vesicles, characterised in that it comprises:
 between 3% and 30% of a lipid concentration formed from a mixture of phospholipids and fatty acids in a molar ratio comprised between 5:1 and 1:1 without presence of polymers or surfactants
 between 70% and 97% of water.
In a preferred embodiment, the lipid gel has:
 a lipid concentration comprised between 3% and 10%
 a molar ratio between phospholipids and fatty acids comprised between 3:1 and 1:1
 a water content comprised between 90% and 97%.

The phospholipid is selected, inter alia, from phosphatidylcholines, phosphatidylserines, phosphatidylglycerol, phosphatidylinositol and phosphatidylethanolamines, preferably being hydrogenated soy phosphatidylcholine.

The fatty acid is a saturated or unsaturated fatty acid with a chain length between 10 and 24 C atoms, with one or more double links; the fatty acid is preferably selected from palmitic acid, stearic acid, oleic acid, linoleic acid, lignoceric acid, eicosapentaenoic acid (EPA) or docosahexaenoic acid (DHA). Oleic acid is the acid used in preferred embodiments.

For use in cutaneous or ocular application systems, the lipid gel incorporates an active ingredient selected from a hydrophilic compound or a lipophilic compound. Some active ingredient options are:
sphingolipids
cholesterol
antioxidants
antibiotics
anti-inflammatories
proteins In order to verify what molecules of a different nature blend well with the system and to be able to monitor the skin, compounds such as for example sodium fluorescein or a lipophilic rhodamine conjugate are used.

A second aspect of the present invention consists of a method for preparing a nanostructured lipid gel as defined earlier, which comprises the steps of:
dispersing the mixture of the lipid components in water without the intervention of polymers or surfactants
forming the gel from the lipid dispersion obtained in the previous step.

The method is carried out without the intervention of polymers or surfactants, wherein the formation of the gel includes the following sub-steps:
adjusting the pH of the lipid dispersion between 5 and 8 with a basic compound
freezing the dispersion with pH adjusted to a temperature equal to or less than −20° C. for a time period of at least 1 minute
thawing and heating the dispersion to a temperature comprised between 5° C. and 90° C.
cooling the gelled dispersion from the previous sub-step at room temperature.

In a preferred embodiment, the dispersion of the mixture is carried out by mixing the lipid components at the specified concentrations and molar ratios in an organic solvent, particularly chloroform. According to the lipids used, other solvents such as ethanol, methanol or mixtures thereof may be required. Next, the solvent is evaporated in a rotary evaporator followed by desiccation and subsequent hydration by adding water in the specified concentration range under agitation conditions and at room temperature. With regard to the pH adjustment of the lipid dispersion, it can be adjusted with a sodium hydroxide solution.

Lastly, a third aspect of the invention consists of the use of a nanostructured lipid gel as defined previously in cutaneous, mucous or ocular application systems.

BRIEF DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION AND EMBODIMENT OF THE INVENTION

Figure 1:
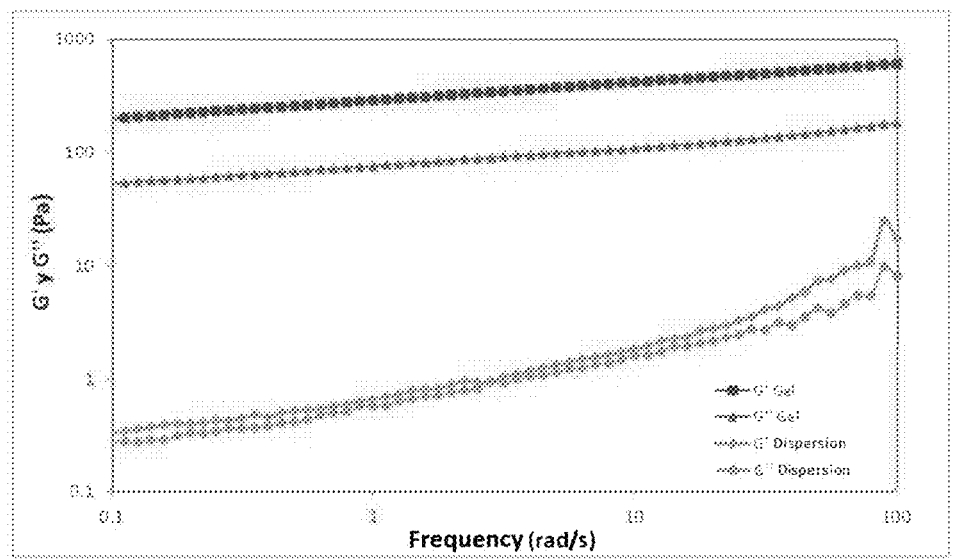
FIG. 1: shows an oscillation frequency sweep to confirm the rheological behaviour of the material as a gel and comparison with the lipid dispersion of the paper by Talló K. et al. (2018).

The main novel feature of the lipid gels object of the present invention is that a mixture formed only by lipids, without the intervention of polymers or surfactants, and that contains a very high water content, up to 97%, is capable of being structured as a gel. As indicated in the discussion of the state of the art, dense emulsion/gel-type systems constituted only by lipids are usually formed at high lipid concentrations (>50%), generating tight packing phases such as cubic or lamellar phases, while the most diluted systems require other compounds such as surfactants, gelling agents or polymers to achieve gel-type rheological behaviour.

Once formed, the gel maintains a semi-rigid structure and exhibits a translucent white colour at room temperature, while the gel becomes fluid and transparent as of a certain temperature that varies according to the lipid composition of the system and which can be as of 5° C. It should be noted that this process is reversible and the gel structure is recovered once cooled below that variable temperature in accordance with the lipid composition of the system.

Composition

The phospholipids most frequently used to prepare the systems form part of the group of phosphatidylcholines and are a commercial product obtained from soy lecithin known as "hydrogenated soy phosphatidylcholine (HSPC)".

In order to form the gel, the HSPC is mixed with the oleic acid (OA) in a molar ratio of 3:1 and is adjusted to a pH of 5-8 using sodium hydroxide. The pH range is a decisive factor to correctly formulate the gel. The total lipid concentration by weight (HSPC+OA) has been established as optimum at 5%, since very diluted systems (<3%) are not formed, while more concentrated systems (>10%) are difficult to disperse using conventional methods.

In order to form the gels, a freezing process followed by a heating process of the lipid dispersion is required.

With other phospholipids with different HSPC features, particularly different polar heads and different alkyl chains, and with fatty acids other than oleic acid, the results obtained are equivalent, although the formation and reversibility conditions vary in accordance with the physico-chemical parameters of the lipids. The molar ratio between the lipids present in the mixture may vary with similar results. Although the lipid concentration with which most of our results were obtained was 5%, higher concentrations also give rise to the formation of these gels.

Table 1 shows various examples of gel-forming systems with a description of their aspect and behaviour:

TABLE 1

| Composition Molar Ratio | Lipid Concentration (%) | Aspect/Behaviour |
| --- | --- | --- |
| HSPC/LA 3/1 | 5 | Semi-transparent/Gel |
| HSPC/SA 3/1 | 5 | Semi-transparent/Gel |
| DPPC/OA 3/1 | 5 | Transparent/Gel |
| DMPC/OA 3/1 | 5 | Transparent/Fluid Gel |

HSPC: hydrogenated soy phosphatidylcholine
DPPC: dipalmitoylphosphatidylcholine
DMPC: dimyristoylphosphatidycholine
OA: oleic acid
LA: lignoceric acid
SA: stearic acid Characterisation Rheology The main objective of this technique is to determine whether the samples obtained behaved rheologically as a gel.

An oscillation amplitude sweep ("Strain Sweep") was initially performed wherein the linear viscoelastic region (LVR) was determined in order to be able to work with reliable parameters. Next, an oscillation frequency sweep ("Frequency Sweep") was performed to evaluate the viscous and elastic properties of the material.

As mentioned in the discussion of the state of the art, in the paper by Talló, K; López, O. and col. *Vesicular nanostructures composed of oleic acid and phosphatidylcholine: Effect of pH and molar ratio*; Chemistry and Physics of Lipids 213 (2018) 96-101 presents an aqueous vesicle dispersion that behaves as a viscous liquid at macroscopic level. This system clearly differs rheologically and structurally from the nanostructured lipid gel of the present invention. Although both have the same chemical components, the method of preparation allows the system described in the present application to be structured as a gel and not as a simple dispersion. At first glance it can be observed how the gel maintains a rigid structure while the aqueous vesicle dispersion flows in its receptacle. In order to show that they are different products, with differentiated rheological behaviour, an oscillation sweep was performed on both systems under the same pH, concentration and temperature conditions (FIG. 1).

As can be seen in FIG. 1, the gel (invention) and the lipid dispersion (prepared with the protocol described in the paper by Talló et al. 2018) have very different rheological behaviour. The values of the elastic module (G') and the viscous module (G") of the gel exceed the G' and G" values of the vesicle dispersion described in the paper by two orders of magnitude. This means that the lipid gel object of the present invention is much more structured at microscopic level, giving the product greater consistency and rigidity. It can also be observed that the G' value of the gel is clearly higher than the G" value, which indicates that the elastic behaviour (solid) prevails over the viscous behaviour. In contrast, for the vesicle dispersion the G' and G" values are nearly identical, overlapping at some point, which indicates that the viscous behaviour of the dispersion is comparable to the elastic behaviour.

Electron Microscopy

Figure 2:
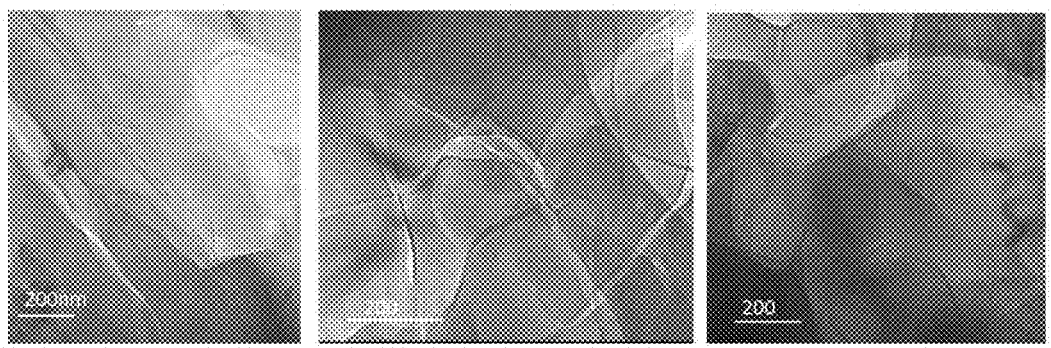
FIG. 2: shows transmission electron cryomicroscopy (CryoTEM) images wherein the lamellar and vesicular structure of the gels can be observed.

In order to observe the nanoscopic structure of the gels, the samples were cryofixed following different methods. In some cases, a fracture was forced through the sample in order to reveal possible lamellar or vesicular-type aggregates. The samples were observed by means of transmission electron cryomicroscopy (CryoTEM). FIG. 2 shows different images of the sample wherein stacks of extended flat membranes combined with unilamellar vesicles can be observed. The laminae were extended to micron level, although thickness is adjusted to a lipid membrane. The vesicles are interspersed between the laminae and exhibit sizes approximately between 100-150 nm in diameter.

Small-Angle X-Ray Scattering (SAXS)

Figure 3A:
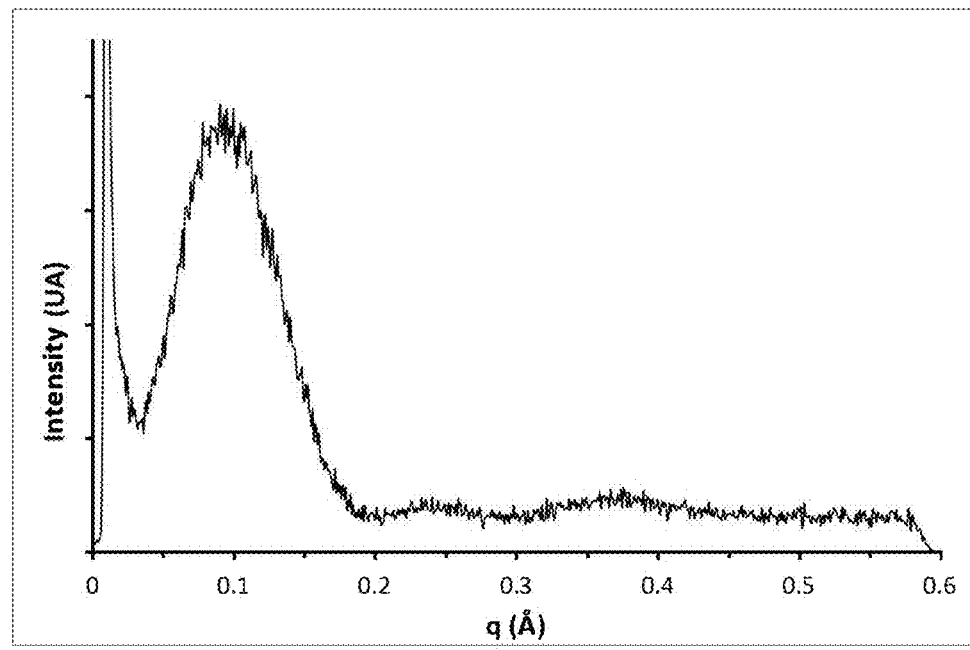
FIG. 3A: shows a small-angle X-ray scattering profile (SAXS).
Figure 3B:
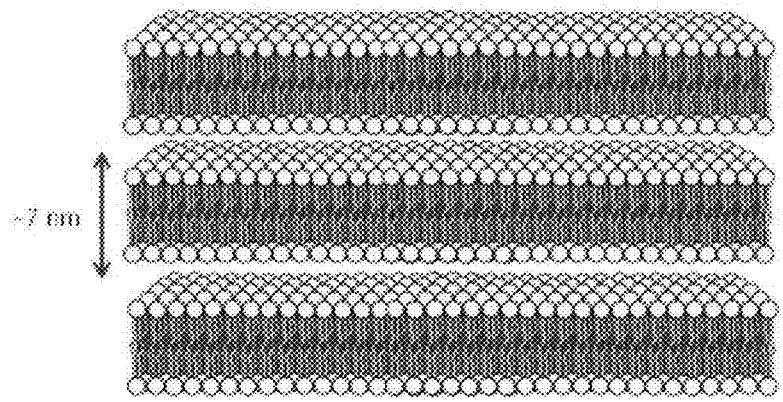
FIG. 3B: shows a lamellar structure.

This technique was used to determine that the gel is composed of a lamellar structure. This fact can be observed from the small-angle X-ray scattering profile (SAXS) shown in FIG. 3A. In said figure, a broadband corresponding to spacing distance of approximately 7 nm is observed, calculated on the basis of the scattering vector q and the equation $q_n = 2n\pi/d$, wherein d is the spacing distance, n is the scattering order and q is the scattering vector. The location of the following Bragg bands in positions 3q and 4q indicate a multi-lamellar structure that would have a spacing of 7 nm and an organisation such as that shown in FIG. 3B.

Wide-Angle X-Ray Scattering (WAXS)

Figure 4A:
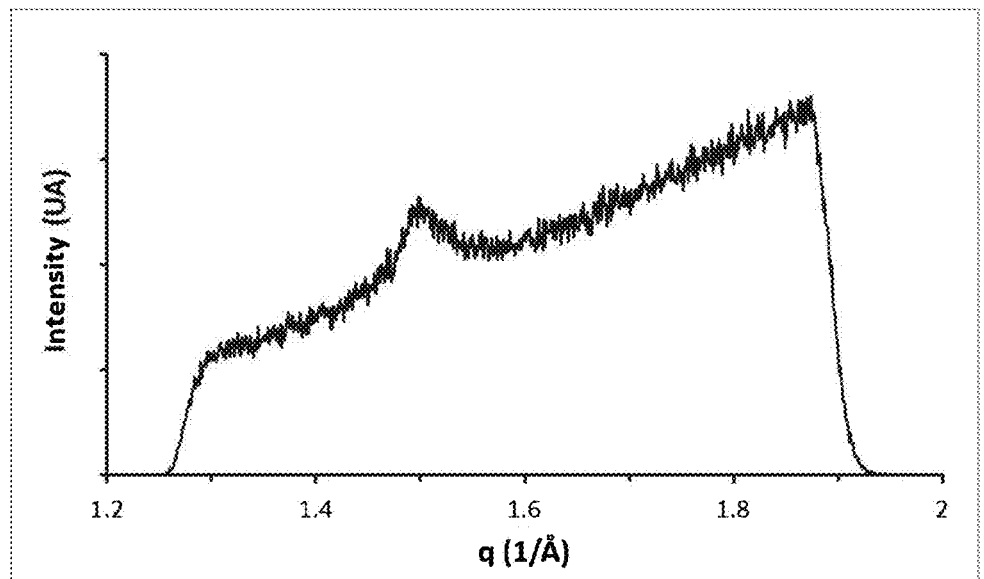
FIG. 4A: shows a wide-angle X-ray scattering profile (WAXS).
Figure 4B:
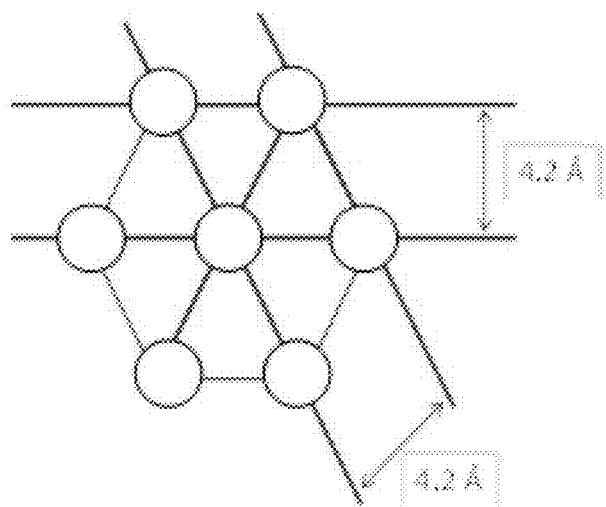
FIG. 4B: shows hexagonal packing.

The lateral packing of the phospholipids was determined using this technique. As shown in FIG. 4A, there is only one peak corresponding to a spacing value between polar heads of 4.2 Å, which would indicate that it is hexagonal packing such as shown in FIG. 4B.

Application on the Skin

The structural consistency of a gel represents a clear advantage over a liquid lipid dispersion such as that of Talló K. et al. (2018), since it facilitates topical application. This factor is evident bearing in mind that most commercial products for cutaneous application are creams or gels. Structurally, the lamellar organisation of lipid membranes confers greater stability to the product, while a vesicular system such as that described in Talló et al. (2018) tends to aggregate and flocculate if stabilisers are not added. Furthermore, microscopic structural differences may imply a major difference in the field of pharmacokinetics and drug administration.

Cutaneous Permeation

In order to evaluate the potential of these gels as cutaneous application systems, an in vitro permeation assay was conducted on pig skin and observations were made using fluorescence microscopy.

Two gels were formed which were applied to the skin surface. One of them was formed by incorporating a red fluorescent probe (Rhodamine B) in order to observe in which areas of the skin the gel-forming phospholipids are retained. In the other gel, a fluorescent green probe (fluorescein) was added in the aqueous phase with the aim of simulating a possible water-soluble active ingredient incorporated to the gel. The gel was gently applied to the skin and left to permeate overnight at 37° C. in a humid environment. Next, the skin was cut into sections and the cells marked in blue in order to distinguish the different skin layers.

Figure 5:
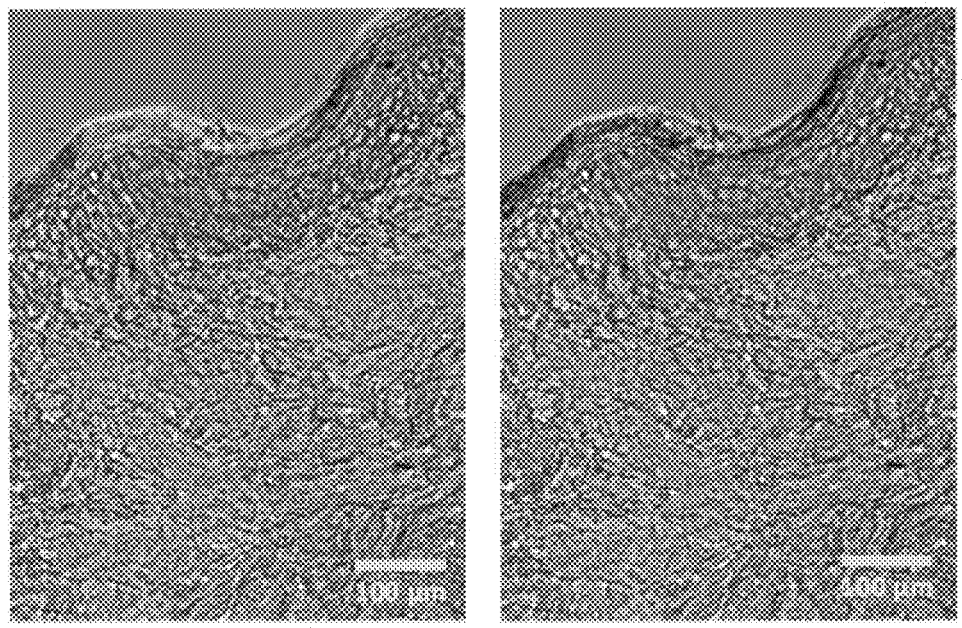
FIG. 5: shows a sectional view of the skin wherein the retention of the lipid system (red) and epidermis marking (blue) can be observed.
Figure 6:
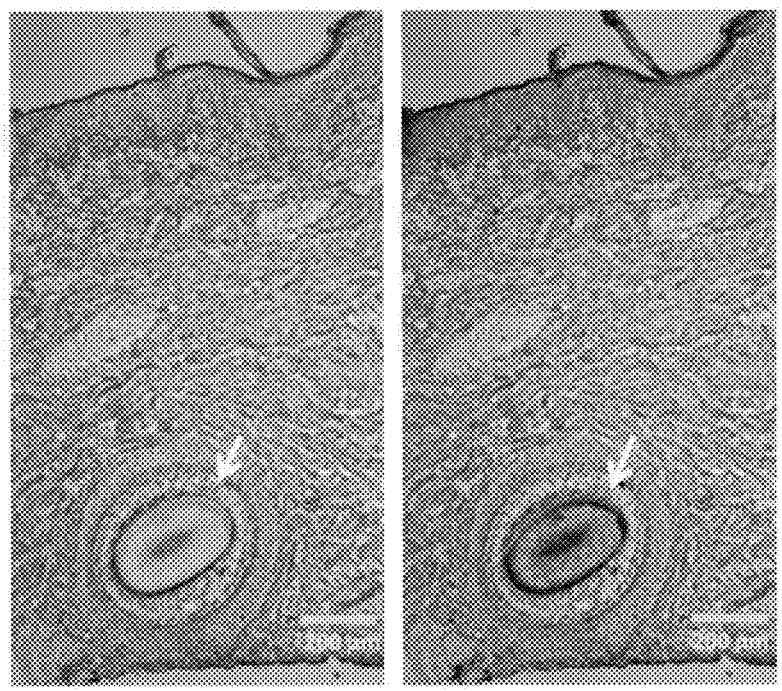
FIG. 6: shows a sectional view of the skin with a follicle (white arrow) wherein the permeation of the fluorescein (green) and epidermis marking (blue) can be observed.

FIG. 5 shows how the lipid gel matrix (red) is retained at the top of the stratum corneum (outermost layer of the skin) without reaching the epidermis (blue). FIG. 6 shows how the fluorescein dissolved in the aqueous phase of the gel (green) is capable of permeating the skin, covering the entire stratum corneum and epidermis. Similarly, it can be observed how it is also capable of going down the follicle, staining the hair (blue arrow). It should be noted that a control was carried out using an aqueous solution with fluorescein (without incorporating the gel) and it was only slightly incorporated in the stratum corneum. Therefore, the gel stimulated the passage of this molecule (fluorescein) through the skin.

These results show that the formation of gels formed by combining phospholipids and oleic acid in water having a very high water content (up to 97%) is possible. These gels lack usual gelling molecules such as polymers or surfactants and the structure and fluidity thereof respond reversibly to temperature and pH. They are also capable of transporting at least one hydrophilic substance within the skin and also to the follicles.

Their particular organisation, with part of the water trapped in vesicles and these vesicles trapped or interspersed between extended laminae, makes them very adequate as systems for incorporating molecules of a different polar nature in different compartments. Their exclusively lipid composition ensures high biocompatibility. Their rheological behaviour enables the easy topical and ocular application thereof and their ability to respond to biological parameters indicates their potential biomedical applications.

Healing Effect

In order to evaluate the potential healing effect of the gel, wound healing studies were carried out on ex-vivo skin explants.

An injury was made to the recently extracted pig skin using a dermatological punch. The wound skin explants were seeded in culture wells using DMEM as culture medium supplemented with FBS, antibiotics and L-glutamine. The explants were maintained under these culture conditions for 14 days. During this period, the injury made to the skin explants was treated with the gel every two days. For comparison purposes injured explants were kept under culture and untreated.

After 14 days, the explants were frozen in liquid nitrogen embedded in OCT. 8-micron cuts were made in the skin using a cryostat. Said sections were stained with eosin and haematoxylin and were observed with an optical microscope.

Figure 7:
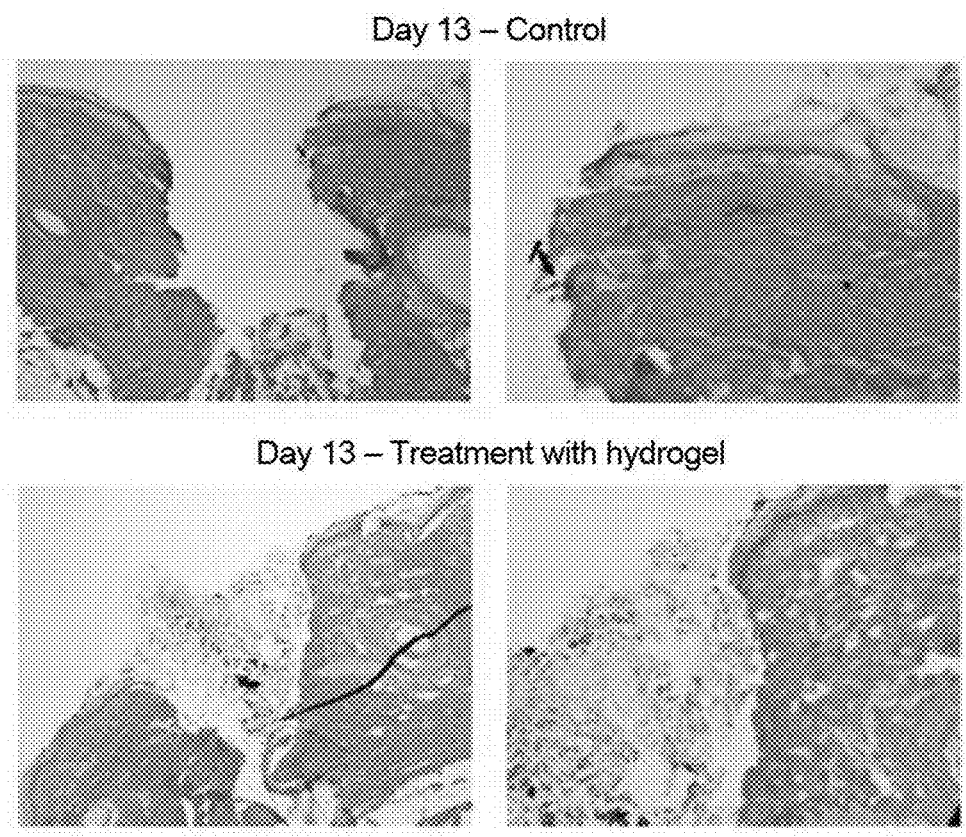
FIG. 7: Effect of the gel on the injury.

In FIG. 7 the difference between the injuries treated with the gel and those not treated can be observed. It can be observed that the lipid gel matrix (stained blue with haematoxylin) remains in the injury. Additionally, a certain re-epithelisation and closure of the injury in treated injuries with respect to untreated injuries can be observed. The rheological behaviour of the gel makes it easy to apply and be confined in the area of application. Its structure, large interconnected vesicles, may act as a medium for the skin cells to grow on, stimulating the tissue healing process. The large lamellae could also favour the growth of new cells and, additionally, because of being lamellae formed by lipid bilayers that are very similar in structure to the lipid matrix of the dermal stratum corneum, they could protect the wound and stimulate the adequate recovery of the barrier function. Once the wound is healed, or during the healing process, the gel structure will become disassembled and the gel components, lipids and water, fully biocompatible, can be integrated in the tissue structure.

Eye Irritation Assay

With the aim of proposing potential uses of the gel in ocular applications, the possible eye irritation of this material was studied by means of a HET-CAM test.

The gel formed from HSPC and OA with a molar ratio of 3:1 and a total lipid concentration of 5% was directly applied to the chorioallantoic membrane of a chicken egg due to its similarity to the human cornea. The appearance of vascular lesion or clotting in response to a compound is the basis for using this technique as an indicator of the probability that a substance may harm the mucous membranes, especially the cornea of the human eye, in vitro.

In order to execute the method, the egg shell is carefully removed, moistening the membrane with a NaCl solution at 37° C. Next, the NaCl is removed and the white membrane is removed without harming any blood vessel.

Next, the gel sample is applied and the appearance of haemorrhage (H), vasoconstriction (V) and/or clotting (C) can be observed for 5 minutes.

Lastly, the Ocular Irritation Index (OII) is estimated using the following formula:

$$OII = \frac{(301 - H) \cdot 5}{300} + \frac{(301 - V) \cdot 5}{300} + \frac{(301 - C) \cdot 9}{300}$$

H, V and C are the time in seconds when this change appears. If there is no alteration, they are equal to 300. The result obtained from the formula can be interpreted on the basis of Table 2:

TABLE 2

| OII | Classification |
|---|---|
| 0-0.9 | Practically non-irritating |
| 1-4.9 | Mildly irritating |
| 5-8.9 | Moderately irritating |
| 9-21 | Irritating |

The results obtained are indicated in Table 3:

TABLE 3

| Egg weight (g) | Sample | Haemorrhage time (s) | Vasoconstriction time (s) | Clotting time (s) | OII | Classification |
|---|---|---|---|---|---|---|
| 59.4 | NaOH | 28 | 13 | 20 | 17.79 | Irritating |
| 57.7 | 1% SDS | 110 | 0 | 0 | 3.23 | Mildly irritating |
| 67.8 | 5% gel | 0 | 0 | 0 | 0.07 | Practically non-irritating |
| 62.4 | 2.5% gel | 0 | 0 | 0 | 0.07 | Practically non-irritating |

Both the initial formulation and the diluted formulation proved to be non-irritating, due to which it can be affirmed that the gel does not cause eye irritation.

The invention claimed is:

1. A nanostructured lipid gel in the form of interspersed laminae and vesicles, comprising:
   between 3% and 30% of lipids wherein said lipids consist of a mixture of phospholipids and fatty acids in a molar ratio between 5:1 and 1:1 and between 70% and 97% of water; and
wherein the nanostructured lipid gel does not contain polymers or surfactants.

2. The lipid gel, according to claim 1, wherein:
the lipids content is between 3% and 10%;
the molar ratio between phospholipids and fatty acids is comprised between 3:1 and 1:1; and
the water content is between 90% and 97%.

3. The lipid gel, according to claim 1, wherein the phospholipid is selected from phosphatidylcholines, phosphatidylserines, phosphatidylglycerol, phosphatidylinositol and phosphatidylethanolamines.

4. The lipid gel, according to claim 3, wherein the phospholipid is hydrogenated soy phosphatidylcholine.

5. The lipid gel, according to claim 1, wherein the fatty acid is a saturated or unsaturated fatty acid with a chain length between 10 and 24 C atoms, wherein the unsaturated fatty acid has one or more double bonds.

6. The lipid gel, according to claim 5, wherein the fatty acid is selected from palmitic acid, stearic acid, oleic acid, linoleic acid, lignoceric acid, eicosapentaenoic acid (EPA) or docosahexaenoic acid (DHA).

7. The lipid gel, according to claim 6, wherein the fatty acid is oleic acid.

8. The lipid gel, according to claim 1, further comprising an active ingredient selected from a hydrophilic compound or a lipophilic compound.

9. The lipid gel, according to claim 8, wherein the active ingredient is a sphingolipid, cholesterol, an antioxidant, an antibiotic, an anti-inflammatory, a protein or combinations thereof.

10. The lipid gel, according to claim 1, further comprising sodium fluorescein.

11. The lipid gel, according to claim 1, further comprising a lipophilic rhodamine conjugate.

12. A cutaneous, mucous or ocular application system comprising the nanostructured lipid gel as defined in claim 1.

13. A method for preparing a nanostructured lipid gel, as defined in claim 1, which comprises the steps of:
a) dispersing the lipids consisting in a mixture of phospholipids and fatty acids in water wherein the nanostructured lipid gel does not contain polymers or surfactants;
b) forming the gel from the lipid dispersion obtained in the previous step a), wherein the nanostructured lipid gel does not contain polymers or surfactants, wherein the formation of the gel comprises the following sub-steps:
b1) adjusting the pH of the lipid dispersion to between 5 and 8 with a basic compound;
b2) freezing the dispersion with pH adjusted to a temperature equal to or less than −20° C. for a time period of equal to or greater than 1 minute;
b3) thawing and heating the dispersion to a temperature comprised between 5° C. and 90° C.; and
b4) leaving the dispersion from the previous sub-step b3) at room temperature, thus obtaining the nanostructured lipid gel.

14. The method for preparing a nanostructured lipid gel, according to claim 13, wherein the dispersion of the mixture is carried out by mixing the lipid components at the specified concentrations and molar ratios in an organic solvent and evaporation thereof in a rotary evaporator, followed by desiccation and subsequent hydration by adding water in the specified concentration range under agitation conditions and at room temperature.

15. The method for preparing a nanostructured lipid gel, according to claim 14, wherein the organic solvent is chloroform and in that the pH adjustment of the lipid dispersion is carried out using a sodium hydroxide solution.

* * * * *